United States Patent
Ruchti et al.

(10) Patent No.: US 7,383,069 B2
(45) Date of Patent: *Jun. 3, 2008

(54) METHOD OF SAMPLE CONTROL AND CALIBRATION ADJUSTMENT FOR USE WITH A NONINVASIVE ANALYZER

(75) Inventors: Timothy L. Ruchti, Gilbert, AZ (US); Kevin H. Hazen, Gilbert, AZ (US); Thomas B. Blank, Chandler, AZ (US)

(73) Assignee: Sensys Medical, Inc., Chandler, AZ (US)

( * ) Notice: Subject to any disclaimer, the term of this patent is extended or adjusted under 35 U.S.C. 154(b) by 381 days.

This patent is subject to a terminal disclaimer.

(21) Appl. No.: 10/849,422

(22) Filed: May 18, 2004

(65) Prior Publication Data

US 2005/0014997 A1    Jan. 20, 2005

Related U.S. Application Data

(63) Continuation-in-part of application No. 10/384,023, filed on Mar. 7, 2003, now Pat. No. 7,010,336, which is a continuation-in-part of application No. 10/170,921, filed on Jun. 12, 2002, now Pat. No. 7,206,623, which is a continuation-in-part of application No. 09/630,201, filed on Aug. 1, 2000, now Pat. No. 6,871,169, which is a continuation-in-part of application No. 09/610,789, filed on Jul. 6, 2000, now abandoned, application No. 10/849,422, which is a continuation-in-part of application No. 09/563,782, filed on May 2, 2000, now Pat. No. 6,415,167, application No. 10/849,422.

(60) Provisional application No. 60/472,613, filed on May 21, 2003.

(51) Int. Cl.
*A61B 5/1455* (2006.01)

(52) U.S. Cl. .................. 600/331; 600/310; 600/322
(58) Field of Classification Search ............... 600/316, 600/331, 344; 250/339.09
See application file for complete search history.

(56) References Cited

U.S. PATENT DOCUMENTS 4,033,054 A    7/1977  Fukuoka (Continued)

FOREIGN PATENT DOCUMENTS

DE          2640987         3/1978

(Continued)

OTHER PUBLICATIONS

Webster's II New riverside University Dictionary, Riverside Publishing Company. 1994, p. 1000.

(Continued)

*Primary Examiner*—Eric F. Winakur
*Assistant Examiner*—Etsub D Berhanu
(74) *Attorney, Agent, or Firm*—Michael A. Glenn; Glenn Patent Group

(57) ABSTRACT

A method and apparatus for easing the use of an optically based noninvasive analyzer is presented. More particularly, a simplified algorithm is used that removes the daily requirement of collecting and using a noninvasive spectrum to update a calibration model. In another embodiment, a guide is used to substantially reduce variation in sample probe placement in relation to a skin tissue sampling site, resulting in the ability to maintain calibration performance with the use of a reference analyte concentration, with or without the use of a reference spectrum collected nearby in time.

3 Claims, 6 Drawing Sheets

U.S. PATENT DOCUMENTS

| | | | |
|---|---|---|---|
| 4,321,930 A | | 3/1982 | Jobsis et al. |
| 4,893,253 A | | 1/1990 | Lodder |
| 5,070,874 A | | 12/1991 | Barnes et al. |
| 5,077,476 A | * | 12/1991 | Rosenthal .............. 250/339.04 |
| 5,170,786 A | | 12/1992 | Thomas et al. |
| 5,252,829 A | | 10/1993 | Nygaard et al. |
| 5,285,783 A | | 2/1994 | Secker |
| 5,299,570 A | | 4/1994 | Hatschek |
| 5,308,982 A | | 5/1994 | Ivaldi et al. |
| 5,348,002 A | | 9/1994 | Caro |
| 5,379,764 A | | 1/1995 | Barnes et al. |
| 5,448,662 A | | 9/1995 | Kittell et al. |
| 5,492,118 A | | 2/1996 | Gratton et al. |
| 5,494,032 A | | 2/1996 | Robinson et al. |
| 5,506,482 A | | 4/1996 | Teramatsu et al. |
| 5,507,288 A | | 4/1996 | Bocker et al. |
| 5,518,694 A | | 5/1996 | Bentsen |
| 5,548,674 A | | 8/1996 | Rondeau |
| 5,606,164 A | | 2/1997 | Price et al. |
| 5,619,195 A | | 4/1997 | Allen et al. |
| 5,636,634 A | | 6/1997 | Kordis et al. |
| 5,638,816 A | | 6/1997 | Kiami-Azarbayjany et al. |
| 5,655,530 A | | 8/1997 | Messerschmidt |
| 5,661,843 A | | 8/1997 | Rickenbach et al. |
| 5,671,317 A | | 9/1997 | Weishaupt et al. |
| 5,725,480 A | | 3/1998 | Oosta et al. |
| 5,743,262 A | | 4/1998 | Lepper, Jr. et al. |
| 5,747,806 A | | 5/1998 | Khalil et al. |
| 5,769,076 A | | 6/1998 | Maekawa et al. |
| 5,825,488 A | | 10/1998 | Kohl et al. |
| 5,830,132 A | | 11/1998 | Robinson |
| 5,840,020 A | * | 11/1998 | Heinonen et al. ........... 600/309 |
| 5,869,075 A | | 2/1999 | Krzysik |
| 5,876,121 A | | 3/1999 | Burns et al. |
| 5,879,373 A | | 3/1999 | Boecker et al. |
| 5,891,021 A | | 4/1999 | Dillon et al. |
| 5,956,150 A | | 9/1999 | Kanne |
| 5,978,691 A | | 11/1999 | Mills |
| 5,978,697 A | | 11/1999 | Mills |
| 6,014,756 A | | 1/2000 | Raley |
| 6,040,578 A | | 3/2000 | Malin et al. |
| 6,045,511 A | | 4/2000 | Ott et al. |
| 6,115,673 A | | 9/2000 | Malin et al. |
| 6,119,026 A | | 9/2000 | McNulty et al. |
| 6,152,876 A | | 11/2000 | Robinson et al. |
| 6,157,041 A | * | 12/2000 | Thomas et al. ............. 250/573 |
| 6,219,132 B1 | | 4/2001 | Scharlack et al. |
| 6,240,306 B1 | | 5/2001 | Rohrscheib et al. |
| 6,280,381 B1 | | 8/2001 | Malin et al. |
| 6,341,257 B1 | | 1/2002 | Haaland |
| 6,381,489 B1 | | 4/2002 | Ashibe |
| 6,415,167 B1 | * | 7/2002 | Blank et al. ................ 600/344 |
| 6,421,549 B1 | | 7/2002 | Jacques |
| 6,441,388 B1 | | 8/2002 | Thomas et al. |
| 6,528,809 B1 | | 3/2003 | Thomas et al. |
| 6,585,370 B2 | | 7/2003 | Zelman |
| 6,631,282 B2 | * | 10/2003 | Rule et al. .................. 600/344 |
| 2003/0040663 A1 | | 2/2003 | Rule et al. |
| 2003/0069484 A1 | | 4/2003 | Blank et al. |

FOREIGN PATENT DOCUMENTS

| | | |
|---|---|---|
| EP | 419222 A2 | 3/1991 |
| JP | 2002/535023 T | 10/2002 |
| WO | WO 96/28084 | 9/1996 |
| WO | WO 96/32631 | 10/1996 |
| WO | WO 97 05819 | 2/1997 |
| WO | WO 97/06418 | 2/1997 |
| WO | WO 00/22985 | 4/2000 |
| WO | WO 00/42907 | 7/2000 |
| WO | WO 00 76575 | 12/2000 |

OTHER PUBLICATIONS

W. Cheong, et al., "A Review Of The Optical Properties Of Biological Tissues," Dec. 1990, IEEE Journal of Quantum Electronics, vol. 26, No. 12, pp. 2166-2185.

J. Conway, et al., "A New Approach For The Estimation Of Body Composition: Infrared Interactance," Dec. 1984, The American Journal of Clinical Nutrition, vol. 40, pp. 1123-1140.

K. Danzer, et al., "Near-Infrared Diffuse Reflection Spectroscopy For Noninvasive Blood-Glucose Monitoring," 1998, LEOS Newsletter, vol. 12, No. 2, pp. 9-11.

"Diabetes Statistics," Nov. 1997, Publication No. 98-3926, National Institutes of Health, Bethesda, MD.

N. Draper, et al., "Applied Regression Analysis," 1981, John Wiley and Sons, 2$^{nd}$ Ed., New York.

The Diabetes Control and Complications Trial Research Group, "The Effect Of Intensive Treatment Of Diabetes On The Development," 1993, New England Journal of Med., vol. 329, pp. 977-986.

A. Guyton, et al., "Textbook of Medical of Physiology: Exchange of Nutrients and Other Substances," 1996, Philadelphia, W.B. Saunders Company, 9$^{th}$ Ed.

C. Fischbacker, et al., "Enhancing Calibration Models For Noninvasive Near-Infrared Spectroscopic Blood Glucose Determinations," 1997, Fresenius Journal of Anal Chem., vol. 359, pp. 78-82.

P. Geladi, et al., "Linearization And Scatter-Correction For Near-Infrared Reflectance Spectra Of Meat," Applied Spectroscopy, 1985, vol. 39, pp. 491-500.

P. Geladi, et al., "Partial Least-Squares Regression: A Tutorial," 1986, Analytica Chimica Acta, 185, pp. 1-17.

S. Haykin, "Neural Networks: A Comprehensive Foundation," 1994, Prentice Hall, Upper Saddle River NJ.

Hazen, Kevin H. "Glucose Determination in Biological Matrices Using Near-Infrared Spectroscopy," 1995, Doctoral Dissertation, University of Iowa.

H. Heise, et al., "Effect Of Data Pretreatment On The Noninvasive Blood Glucose Measurement By Diffuse Reflectance Near-IR Spectroscopy," 1994, SPIE Proc, vol. 2089, pp. 114-115, 1994.

H. Heise, et al., "Noninvasive Blood Glucose Sensors Based On Near-Infrared Spectroscopy," 1994, Artif Org, vol. 18, pp. 429-447.

S. Homma, et al., "Influence Of Adipose Tissue Thickness In Near Infrared Spectroscopic Signals In The Measurement Of Human Muscle," Oct. 1996, Journal of Biomedical Optics, vol. 1., No. 4, pp. 418-424.

T. Isaksson, et al., "Piece-Wise Multiplicative Scatter Correction Applied to Near-Infrared Diffuse Transmittance Data from Meat Products," 1993, Applied Spectroscopy, vol. 47, pp. 702-709.

T. Isaksson, et al., "Optimised Scaling (OS-2) Regression Applied To Near Infrared Diffuse Spectroscopy Data From Food Products," 1993, Near Infrared Spectroscopy, vol. 1, pp. 85-97.

S. Jacques, "Origins of tissue optical properties in the UVA, Visible and NIR Regions," Mar. 18-22, 1996, Optical Society of America, Topical Meeting, Orlando FL.

K. Jagemann, et al., "Application Of Near-Infrared Spectroscopy For Noninvasive Determination Of Blood/Tissue Glucose Using Neural Network," 1995, Z Phys. Chem., vol. 191S, pp. 179-190.

O. Khalil, "Spectroscopic And Clinical Aspects Of Noninvasive Glucose Measurements," 1999, Clin. Chem., vol. 45, pp. 165-177.

R. Marbach, et al., "Noninvasive Blood Glucose Assay By Near-Infrared Diffuse Reflectance Spectroscopy Of The Human Inner Lip," 1993, Appl Spectrosc, vol. 47, pp. 875-881.

R. Marbach, et al., "Optical diffuse reflectance accessory for measurements of skin tissue by near-infrared spectroscopy," 1995, Applied Optics, vol. 34, No. 4, pp. 610-621.

H. Martens, et al., "Extended Multiplicative Signal Correction And Spectral Interference Subtraction: New Preprocessing Methods For Near Infrared Spectroscopy," 1991, J. Pharm Biomed Anal, vol. 9, pp. 625-635.

H. Martens, et al., "Multivariate Calibration," 1989, John Wiley and Sons, New York.

D.L. Massart, et al., "Chemometrics," 1990, New York: Elsevier Science Publishing Company, Inc.

U. Muller, et al., "Noninvasive Blood Glucose Monitoring By Means Of New Infrared Spectroscopic Methods For Improving The Reliability Of The Calibration Models," 1997, Int J Artif Organs, vol. 20, pp. 285-290.

A.V. Oppenheim, et al., "Digital Signal Processing," 1975, Englewood Cliffs, NJ: Prentice Hall, pp. 195-271.

M. Otto, "Chemometrics," 1999, Weinheim: Wiley-VCH.

A. Profio, "Light Transport in Tissue," Jun. 1989, Applied Optics, vol. 28, No. 12, pp. 2216-2222.

M. Robinson, et al., "Noninvasive Glucose Monitoring In Diabetic Patients: A Preliminary Evaluation," 1992, Clin. Chem., vol. 38, pp. 1618-1622.

Rook, et al., "The Normal Skin," 1972, Textbook of Dermatology, 2nd Ed., Blackwell Scientific, Oxford, pp. 4-24.

A. Savitzky, et al., "Smoothing and Differentiation of Data by Simplified Least Squares Procedures," 1964 Anal. Chem., vol. 36, No. 8, pp. 1627-1639.

ST. Sum, Spectral Signal Correction for Multivariate Calibration, Summer 1998, Doctoral Dissertation, University of Delaware.

M. Van Gernert, et al., "Skin Optics," Dec. 1989, IEEE Transactions on Biomedical Engineering, vol. 36, No. 12, pp. 1146-1154.

S. Wilson, et al., "A Tissue Heat Transfer Model For Relating Dynamic Skin Temperature Changes To Physiological Parameters," 1988, Phys. Med. Biol., vol. 33, pp. 894-897.

R. Anderson, et al., "The Optics Of Human Skin," 1981, Journal of Investigative Dermatology, vol. 7, No. 1, pp. 13-19.

B. Wilson, et al., "Optical Reflectance And Transmittance Of Tissues: Principles And Applications," IEEE Journal of Quantum Electronics, vol. 26, No. 12, pp. 2186-2199.

R.J. Barnes, et al., "Standard Normal Variate Transformation And De-Trending Of Near-Infrared Diffuse Reflectance Spectra," 1989, Applied Spectroscopy, 43, pp. 772-777.

K.R. Beebe, et al., "Chemometrics: A Practical Guide," 1998, New York: John Wiley & Sons, Inc.

D. Benaron, et al., "Imaging (NIRI) And Quantitation (NIRS) In Tissue Using Time-Resolved Spectrophotometry: The Impact Of Statically And Dynamically Variable Optical Path Lengths," 1993, SPIE, 1888, pp. 10-21.

T. Blank, et al., "The Use Of Near-Infrared Diffuse Reflectance For The Noninvasive Prediction Of Blood Glucose," Oct. 1999, IEEE Lasers and Electro-Optics Society Newsletter, vol. 13 p. 5.

J. Burmeister, et al., "Human Noninvasive Measurement Of Glucose Using Near Infrared Spectroscopy [abstract]," 1998, Pittcon, New Orleans, LA.

Mark, et al., "Linearity in Calibration—Act II, Scene, II," Jan. 1999, Spectroscopy, vol. 14, No. 1, pp. 16-17.

Arnold et al., "Determination of Physiological Levels of Glucose in an Aqueous Matrix with Digitally Filtered Fourier Transform Near-Infrared Spectra," 1990, Anal. Chem., vol. 62.

Arnold et al., "spectroscopic-based glucose sensors," Unknown Date, Ohio University.

Small, et al., "Strategies for Coupling Digital Filtering with Partial Least-Squares Regression: Application to the Determination of Glucose in Plasma by Fourier Transform Near-Infrared Spectroscopy," 1993, Anal. Chen., vol. 65.

Hazen, et al., "Temperature-Insensitive Near-Infrared Spectroscopic Measurement of Glucose in Aqueous Solutions," 1994, Applied Spectroscopy, vol. 48, No. 4.

Hazen, "Glucose Determination in Biological Matrices Using Near-Infrared Spectroscopy," Aug. 1995, University of Iowa Thesis.

Ljung, Lennart, "Systems Identification: Theory for the User," 1999, Prentice Hall, $2^{nd}$ Ed.

* cited by examiner

METHOD OF SAMPLE CONTROL AND CALIBRATION ADJUSTMENT FOR USE WITH A NONINVASIVE ANALYZER

CROSS REFERENCE TO RELATED APPLICATIONS

This application is:

a continuation-in-part of U.S. patent application Ser. No. 10/170,921, filed on Jun. 12, 2002 now U.S. Pat. No. 7,206,623, which is a continuation-in-part of U.S. patent application Ser. No. 09/563,782, filed on May 2, 2000, now U.S. Pat. No. 6,415,167;

a continuation-in-part of U.S. patent application Ser. No. 10/384,023, filed on Mar. 7, 2003 now U.S. Pat. No. 7,010,336, which is a continuation-in-part of U.S. patent application Ser. No. 09/630,201, filed on Aug. 1, 2000 now U.S. Pat. No. 6,871,169, which is a continuation-in-part of U.S. patent application Ser. No. 09/610,789, filed on Jul. 6, 2000 now abandoned; and claims benefit of U.S. provisional patent application Ser. No. 60/472,613, filed on May 21, 2003.

All of the foregoing applications are incorporated herein in their entirety by this reference thereto.

BACKGROUND OF THE INVENTION

1. Field of the Invention

The invention relates to noninvasive determination of analytes in the human body. More particularly, the invention relates to methods of analyte calibration and prediction that adjust for state changes not compensated for with a static calibration model.

2. Description of Related Art

Noninvasive

A spectroscopy based noninvasive analyzer delivers external energy in the form of light to a region of the body where the photons interact with the chemical constituents and physiology of the sampled tissue. A portion of the incident photons are scattered or transmitted out of the body where they are detected. Based upon knowledge of the incident photons and detected photons, the chemical and/or structural basis of the sampled site is elucidated. A distinct advantages of a noninvasive system includes the determination of a chemical constituent concentration in the body without the generation of a biohazard in a pain free manner and with the use of limited consumables. Further the technique allows for multiple analyte concentrations to be determined at one time. Some common examples of noninvasive analyzers are magnetic resonance imaging (MRI), X-rays, pulse oximeters, and noninvasive glucose analyzers. With the exception of X-rays, these determinations are performed with relatively harmless wavelengths of radiation. Examples herein focus on noninvasive glucose concentration determination, but the principles apply to the detection of other analytes, such as fats, proteins, water, and blood or tissue constituents.

Diabetes

Diabetes is a chronic disease that results in improper production and utilization of insulin, a hormone that facilitates glucose uptake into cells. While a precise cause of diabetes is unknown, genetic factors, environmental factors, and obesity appear to play roles. Diabetics have increased risk in three broad categories: cardiovascular heart disease, retinopathy, and neuropathy. Diabetics often have one or more of the following complications: heart disease and stroke, high blood pressure, kidney disease, neuropathy (nerve disease and amputations), retinopathy, diabetic ketoacidosis, skin conditions, gum disease, impotence, and fetal complications. Diabetes is a leading cause of death and disability worldwide. Moreover, diabetes is merely one among a group of disorders of glucose metabolism that also include impaired glucose tolerance, and hyperinsulinemia, or hypoglycemia.

Diabetes Prevalence and Trends

Diabetes is an ever more common disease. The World Health Organization (WHO) estimates that diabetes currently afflicts 154 million people worldwide. There are 54 million people with diabetes living in developed countries. The WHO estimates that the number of people with diabetes will grow to 300 million by the year 2025. In the United States, 15.7 million people or 5.9 percent of the population are estimated to have diabetes. Within the United States, the prevalence of adults diagnosed with diabetes increased by six percent in 1999 and rose by 33 percent between 1990 and 1998. This corresponds to approximately eight hundred thousand new cases every year in America. The estimated total cost to the United States economy alone exceeds $90 billion per year. Diabetes Statistics, National Institutes of Health, Publication No. 98-3926, Bethesda, Md. (November 1997).

Long-term clinical studies show that the onset of diabetes related complications is significantly reduced through proper control of blood glucose concentrations. The Diabetes Control and Complications Trial Research Group, *The effect of intensive treatment of diabetes on the development and progression of long-term complications in insulin-dependent diabetes mellitus*, N Eng J of Med, 329:977-86 (1993); U.K. Prospective Diabetes Study (UKPDS) Group, *Intensive blood-glucose control with sulphonylureas or insulin compared with conventional treatment and risk of complications in patients with type 2 diabetes*, Lancet, 352:837-853 (1998); and Y. Ohkubo, H. Kishikawa, E. Araki, T. Miyata, S. Isami, S. Motoyoshi, Y. Kojima, N. Furuyoshi, M. Shichizi, *Intensive insulin therapy prevents the progression of diabetic microvascular complications in Japanese patients with non-insulin-dependent diabetes mellitus: a randomized prospective 6-year study*, Diabetes Res Clin Pract, 28:103-117 (1995).

A vital element of diabetes management is the self-monitoring of blood glucose concentrations by diabetics in the home environment. However, current monitoring techniques discourage regular use due to the inconvenient and painful nature of drawing blood through the skin prior to analysis. The Diabetes Control and Complication Trial Research Group, supra. As a result, noninvasive measurement of glucose concentration is identified as a beneficial development for the management of diabetes. Implantable glucose concentration analyzers coupled to an insulin delivery system providing an artificial pancreas are also being pursued.

Sampling Methodology

A wide range of technologies serve to analyze the chemical make-up of the body. These techniques are broadly categorized into two groups, invasive and noninvasive. For the purposes of this document, a technology that acquires any biosample from the body for analysis or if any part of the measuring apparatus penetrates into the body, the technology is referred to as invasive.

Invasive: Some examples of invasive technologies for glucose concentration determination in the body are those that analyze the biosamples of whole blood, serum, plasma, interstitial fluid, and mixtures or selectively sampled components of the aforementioned. Typically, these samples are analyzed with electrochemical, electroenzymatic, and/or colorimetric approaches. For example, enzymatic and colorimetric approaches are used to determine the glucose concentration in interstitial fluid samples.

Noninvasive: A number of approaches for determining the glucose concentration in biosamples have been developed that utilize spectrophotometric technologies. These techniques include: Raman and fluorescence, as well as techniques using light from the ultraviolet through the infrared [ultraviolet (200 to 400 nm), visible (400 to 700 nm), near-IR (700 to 2500 nm or 14,286 to 4000 $cm^{-1}$), and infrared (2500 to 14,285 nm or 4000 to 700 $cm^{-1}$)].

Noninvasive Glucose Determination

There exist a number of noninvasive approaches for glucose concentration determination. These approaches vary widely, but have at least two common steps. First, an apparatus is used to acquire a signal from the body without obtaining a biological sample. Second, an algorithm is used to convert this signal into a glucose concentration determination.

One type of noninvasive glucose concentration analyzer is based upon spectra. Typically, a noninvasive apparatus uses some form of spectroscopy to acquire a signal or spectrum of a body part. Utilized spectroscopic techniques include Raman and fluorescence, as well as techniques using light from the ultraviolet through the infrared [ultraviolet (200 to 400 nm), visible (400 to 700 nm), near-IR (700 to 2500 nm or 14,286 to 4000 $cm^{-1}$), and infrared (2500 to 14,285 nm or 4000 to 700 $cm^{-1}$)]. A particular range for noninvasive glucose determination in diffuse reflectance mode is about 1100 to 2500 nm or ranges therein. K. Hazen, *Glucose Determination in Biological Matrices Using Near-Infrared Spectroscopy*, doctoral dissertation, University of Iowa (1995).

Mode

Typically, three modes are used to collect noninvasive spectra: transmittance, transflectance, and/or diffuse reflectance. For example the signal collected, typically being light or a spectrum, is transmitted through a region of the body such as a fingertip, diffusely reflected, or transflected. Transflected here refers to collection of the signal not at the incident point or area (diffuse reflectance), and not at the opposite side of the sample (transmittance), but rather at some point on the body between the transmitted and diffuse reflectance collection areas. For example, transflected light enters the fingertip or forearm in one region and exits in another region typically 0.2 to 5 mm or more away depending on the wavelength used. Thus, light that is strongly absorbed by the body such as light near water absorbance maxima at 1450 or 1950 nm is collected after a small radial divergence and light that is less absorbed such as light near water absorbance minima at 1300, 1600, or 2250 nm is collected at greater radial or transflected distances from the incident photons.

Site

Noninvasive techniques are not limited to using the fingertip as a measurement site. Alternative sites for taking noninvasive measurements include: a hand, finger, palmar region, base of thumb, wrist, dorsal aspect of the wrist, forearm, volar aspect of the forearm, dorsal aspect of the forearm, upper arm, head, earlobe, eye, tongue, chest, torso, abdominal region, thigh, calf, foot, plantar region, and toe.

Instrumentation

While this specification focuses on optical based noninvasive analyzers, it is important to note that noninvasive techniques do not have to be based upon spectroscopy. For example, a bioimpedence meter is considered to be a noninvasive device. Within the context of the invention, any device that reads a signal from the body without penetrating the skin and collecting a biological sample is referred to as a noninvasive glucose analyzer. For example, a bioimpedence meter is a noninvasive device.

Noninvasive glucose concentration determination using a near-infrared analyzer generally involves the illumination with an input element of a small region on the body with near-infrared (NIR) electromagnetic radiation, infrared light in the wavelength range 700 to 2500 nm, or one or more wavelength ranges therein, such as 1100 to 1800 nm. The light is partially absorbed and partially scattered according to its interaction with the constituents of the tissue prior to being reflected back to light collection means optically coupled to a detector or directly to a detector. The detected light contains quantitative information that corresponds to the known interaction of the incident light with components of the body tissue including water, fat, protein, and glucose.

Optical Registration

In an alternate embodiment, the guide provides a means for optical registration. In this embodiment, reflectors or light sensitive elements are placed onto the guide. The optical probe assembly is equipped with light sources and several detectors that allow the position of the guide to be accurately assessed, in either two or three dimensions. In a first configuration, two dimensions (x,y) are assessed and a mechanical stop is used to control the third dimension. In a second configuration, the location of the guide is optically assessed in all three dimensions (x,y,z). Because the position of the guide is constant with respect to the targeted tissue volume, the positional assessment provides accurate information regarding the location of the targeted tissue volume with respect to the optical probe. The registration information provided by such assessment is used to place the tissue site onto the optical probe, or vice versa, through any of the following means:

an operator or user is given a visual or audible signal indicating how to move the tissue site with respect to the optical probe;

a mechanical positioning system is used to position the tissue measurement site with respect to the optical probe; or a mechanical positioning system is used to position the optical probe onto the tissue measurement site.

One skilled in the art will appreciate that a magnetic sensing system can also be readily applied for assessment of the location of the guide with respect to the tissue measurement site.

While previously described embodiments of the invention employ structural features to control temperature and humidity at the tissue measurement site passively, an alternative embodiment incorporates an airflow device, such as a small blower, to evaporate moisture from the fiber optic probe, the contact surface, and the tissue measurement site.

A noninvasive glucose concentration analyzer has one or more beam paths from a source to a detector. Light source types include a blackbody source, a tungsten-halogen source, one or more LED's, and one or more laser diodes. For multi-wavelength spectrometers a wavelength selection device is used or a series of optical filters are used for wavelength selection. Wavelength selection devices include one or more gratings, prisms, and wavelength selective filters. Variation of the source such as varying which LED or diode is firing is also used for wavelength selection. Detectors are in the form of one or more single element detectors or one or more arrays or bundles of detectors. Detector types include InGaAs, PbS, PbSe, Si, MCT, or the like. Detector arrays include InGaAs, PbS, PbSe, Si, MCT, or the like. Light collection optics such as fiber optics, lenses, and mirrors are commonly used in various configurations as an output element within a spectrometer to direct light from the source to the detector by way of a sample.

Calibration

Glucose concentration analyzers require calibration. This is true for all types of glucose concentration analyzers such as traditional invasive, alternative invasive, noninvasive, and implantable analyzers. One fact associated with noninvasive glucose concentration analyzers is that they are secondary in nature, that is, they do not measure blood glucose concentrations directly. This means that a primary method is required to calibrate these devices in order to measure blood glucose concentrations properly. Many methods of calibration exist.

One noninvasive technology, near-infrared spectroscopy, requires that a mathematical relationship between an in-vivo near-infrared measurement and the actual blood glucose concentration is developed. This is achieved through the collection of in-vivo NIR measurements with corresponding blood glucose concentrations that have been obtained directly through the use of measurement tools such as a YSI (YSI INCORPORATED, Yellow Springs, Ohio) blood glucose concentration analyzer or any appropriate and accurate traditional invasive reference device such as the THERASENSE FREESTYLE (THERASENSE, INC., Alameda Calif.) glucose concentration analyzer.

For spectrophotometric based analyzers, there are several univariate and multivariate methods that are used to develop the mathematical relationship between the measured signal and the actual blood glucose concentration. However, the basic equation being solved is known as the Beer-Lambert Law. This law states that the strength of an absorbance/reflectance measurement is proportional to the concentration of the analyte which is being measured, as in Equation 1, $$A = \epsilon b C \tag{1}$$

where A is the absorbance/reflectance measurement at a given wavelength of light, $\epsilon$ is the molar absorptivity associated with the molecule of interest at the same given wavelength, b is the distance that the light travels in the sample, and C is the concentration of the molecule of interest (glucose).

Chemometric calibration techniques extract glucose related signal from the measured spectrum through various methods of signal processing and calibration including one or more mathematical models. The models are developed through the process of calibration on the basis of an exemplary set of spectral measurements known as the calibration set and associated set of reference blood glucose concentrations based upon an analysis of capillary blood, venous blood, or interstitial fluid. Common multivariate approaches requiring an exemplary reference glucose concentration vector for each sample spectrum in a calibration include partial least squares (PLS) and principal component regression (PCR). Many additional forms of calibration or optimization are known to those skilled in the art.

An apparatus for measuring infrared throughput typically includes an energy source emitting infrared energy at multiple wavelengths, an input element, an output element, and a spectrum analyzer. Tissue is irradiated with multiple wavelengths from the input element where at least some of the photons are scattered and absorbed by the tissue. A portion of the photons exit the tissue sample, are collected by the output element, are directed toward a detector, and are detected. The resulting signal is utilized in a model for determining the analyte concentration.

Calibration Maintenance

Multivariate models reduce a complex measurement in a space modeled with a reduced number of factors. Data collected for the creation of the original model is done under a set of conditions. Often this set of conditions changes to the extent that the original model no longer functions adequately. For example, the environmental temperature effects the light collection performance of a spectrometer. In addition to instrumentation and environmental impacts, changes in the sample affect the model. For example, commonly interference concentrations vary outside of those tested or new interferences are introduced. In noninvasive determination of glucose concentration in the body, another key issue with sampling is that the sample is alive and dynamic in nature. This results in updates to the calibration being required.

Prediction

A calibration is used in combination with noninvasive spectra of a subject to determine the analyte concentration of that subject.

Dynamic Properties of Skin

The dynamic properties of skin tissue is an important and largely ignored aspect of noninvasive glucose determinations. At a given measurement site, skin tissue is often assumed to remain static, except for changes in the target analyte and other interfering species. However, variations in the physiological state and fluid distribution of tissue profoundly affect the optical properties of tissue layers and compartments over a relatively short period of time.

Many factors impact the physical and chemical state of skin. These include environmental and physiological factors. A list of such factors includes at least body temperature, environmental temperature, food intake, drug or medicine intake, and applied pressure to a sampling site. An impact on one part of the body will affect many other locations in the body. For example, food intake into the digestive track causes movement of water between internal body compartments. Another example is caffeine or stimulant intake that changes blood pressure or results in dilation of capillaries.

Noninvasive Glucose Determination

There exist a number of reports on noninvasive glucose technologies. Some of these relate to general instrumentation configurations required for noninvasive glucose determination. Others refer to sampling technologies. Those most related to the present invention are briefly reviewed here:

General Instrumentation

P. Rolfe, Investigating substances in a patient's bloodstream, UK Patent Application No. 2,033,575 (Aug. 24, 1979) describe an apparatus for directing light into the body, detecting attenuated backscattered light, and utilizing the collected signal to determine glucose concentrations in or near the bloodstream.

C. Dahne, D. Gross, Spectrophotometric method and apparatus for the non-invasive, U.S. Pat. No. 4,655,225

(Apr. 7, 1987) describe a method and apparatus for directing light into a patient's body, collecting transmitted or back-scattered light, and determining glucose from selected near-IR wavelength bands. Wavelengths include 1560 to 1590, 1750 to 1780, 2085 to 2115, and 2255 to 2285 nm with at least one additional reference signal from 1000 to 2700 nm.

M. Robinson, K. Ward, R. Eaton, D. Haaland, Method and apparatus for determining the similarity of a biological analyte from a model constructed from known biological fluids, U.S. Pat. No. 4,975,581 (Dec. 4, 1990) describe a method and apparatus for measuring a concentration of a biological analyte such as glucose using infrared spectroscopy in conjunction with a multivariate model. The multivariate model is constructed form plural known biological fluid samples.

J. Hall, T. Cadell, Method and device for measuring concentration levels of blood constituents non-invasively, U.S. Pat. No. 5,361,758 (Nov. 8, 1994) describe a noninvasive device and method for determining analyte concentrations within a living subject utilizing polychromatic light, a wavelength separation device, and an array detector. The apparatus uses a receptor shaped to accept a fingertip with means for blocking extraneous light.

R. Barnes, J. Brasch, D. Purdy, W. Lougheed, Non-invasive determination of analyte concentration in body of mammals, U.S. Pat. No. 5,379,764 (Jan. 10, 1995) describe a noninvasive glucose analyzer that uses data pretreatment in conjunction with a multivariate analysis to determine blood glucose concentrations.

S. Malin, G Khalil, Method and apparatus for multi-spectral analysis of organic blood analytes in noninvasive infrared spectroscopy, U.S. Pat. No. 6,040,578 Mar. 21, 2000) describe a method and apparatus for determination of an organic blood analyte using multi-spectral analysis in the near-IR. A plurality of distinct nonoverlapping regions of wavelengths are incident upon a sample surface, diffusely reflected radiation is collected, and the analyte concentration is determined via chemometric techniques.

Temperature

It is a well-known that many physiological constituents have near-IR absorbance spectra that are sensitive in terms of magnitude and location to localized temperature. This has been reported as impacting noninvasive glucose determinations. [see K. Hazen, *Glucose determination in biological matrices using near-infrared spectroscopy*, Doctoral Dissertation, University of Iowa (August, 1995)].

Coupling Fluid

T. Blank, G. Acosta, M. Mattu, S. Monfre, Fiber optic probe guide placement guide, U.S. Pat. No. 6,415,167 (Jul. 2, 2002) describe a coupling fluid of one or more perfluoro compounds where a quantity of the coupling fluid is placed at an interface of the optical probe and measurement site. Perfluoro compounds do not have the toxicity associated with chlorofluorocarbons.

Calibration Adjustment

Several methods have been reported to compensate in some part for the dynamic variation of tissue samples.

One reported method of calibration model generation for noninvasive glucose concentration determination is to model an individual over a short period of time [see K. Hazen, *Glucose determination in biological matrices using near-infrared spectroscopy*, Doctoral Dissertation, University of Iowa (August, 1995); and J. Burmeister, *In-vitro model for human noninvasive blood glucose measurements*, Doctoral Dissertation, University of Iowa (December 1997)]. This approach avoids modeling the differences between patients and therefore cannot be generalized to more individuals. This approach also fails to address the prevalent short-term problem related to physiologically induced variation and no means of compensating for variation related to the dynamic water shifts of fluid compartments is reported.

Another approach to overcome the effect of tissue variation on a model is to use cross-validation. In one study, meal tolerance tests were used to perturb the glucose concentrations of three subjects and calibration models were constructed specific to each subject on single days and tested through cross-validation [see Robinson M. R.; Eaton R. P.; Haaland D. M.; Keep G. W.; Thomas E. V.; Stalled B. R.; and Robinson P. L. *Non-invasive glucose monitoring in diabetic patients: A preliminary evaluation, Clin Chem* 1992;38:1618-22]. This approach models the differences between some patients presumably with the intent of modeling variations so that future subjects are predicted by the original model. This approach also fails to address the prevalent short-term problem related to physiologically induced variation and no means of compensating for variation related to the dynamic water shifts of fluid compartments is reported.

Still another approach to overcome the effect of tissue variation on a model is to use extensive calibration of each subject through a series of glucose perturbations often over an extended period of time such as 2 to 12 weeks. Often these calibration periods are followed by an evaluation period during which a subject goes through one or more additional glucose excursions. The intent is to incorporate into the model an extensive set of conditions covering future conditions when predictions are made. When many excursions are used, this incorporation often occurs over a period of weeks. To date, this extensive calibration and testing protocol has met with limited success.

Yet another method to overcome the effect of tissue variation on a model is to compensate for variation related to the structure and state of the tissue through an intelligent pattern recognition system capable of determining calibration models that are most appropriate for the patient at the time of measurement [see Malin, S. F.; et. al. An Intelligent System for Noninvasive Blood Analyte Prediction, U.S. Pat. No. 6,280,381]. The calibration models are developed from the spectral absorbance of a representative population of patients that have been segregated into groups. The groups or classes are defined on the basis of structural and state similarity such that the variation within a class is small compared to the variation between classes. Classification occurs through extracted features of the tissue absorbance spectrum related to the current patient state and structure.

Still an additional group of approaches to overcome the effect of tissue variation on a model is calibration transfer. A number of pretreatment of spectral data techniques have been employed. A general but incomplete list of these pretreatment steps include trimming, wavelength selection, centering, scaling, normalization, taking an nth derivative ($n \geq 1$), smoothing, Fourier transforming, principle component selection, finite impulse response filtering, linearization, and transformation. This general class of techniques is found to be limiting in terms of noninvasive glucose concentration analyzer requirements.

Still an additional approach to overcome the effect of tissue variation on a model is a group of techniques based upon local centering using a single spectrum [see Lorber et. al., *Local Centering in Multivariate Calibration*, Journal of Chemometrics, 1996, 10, 215-220]. In this method, a spectrum is selected for mean centering the calibration data set that is the closest match (with respect to Mahalanobis distance) to that of the unknown sample spectrum. A separate partial least squares model is then constructed for each unknown sample. This technique does not reduce the spectroscopic variation of the calibration set.

Another approach to overcome the effect of tissue variation on a model is related to the technique of mean centering [see E. Thomas, R. Rowe, Methods and apparatus for tailoring spectroscopic calibration models, U.S. Pat. No. 6,528,809 (Mar. 4, 2003) and E. Thomas, R. Rowe, Methods and apparatus for tailoring Spectroscopic Calibration Models, U.S. Pat. No. 6,157,041 (Dec. 5, 2000)]. This method uses spectrographic techniques in conjunction with an improved subject-tailored calibration model. In calibration data, the model data is modified to reduce or eliminate subject-specific attributes, resulting in a calibration data set modeling within-subject physiological variation and instrument variation. In the prediction phase, the prediction process is modified for each target subject utilizing a minimal number of spectral measurements for each subject. However, this method does not address the key problem of short term physiological and chemical changes related to the dynamic nature of the tissue nor the intra-patient variation related to the heterogeneity of the tissue sample.

E. Thomas, U.S. Pat. No. 6,528,809, supra and E. Thomas, U.S. Pat. No. 6,157,041, supra use an infrared based noninvasive glucose concentration analyzer to obtain absorbance spectra of human tissue in combination with a model that is periodically corrected with the use of both a spectrum collected from the tested subject and an invasive reference glucose concentration determination collected from the tested subject. The technique employed is loosely referred to as mean centering, though the subtracted spectrum is not the mean spectrum and the glucose value is used to correct an offset in the predicted value. Collection of the reference spectrum is time consuming, requires some expertise on the part of the user, requires data collection software, and requires a microprocessor or other computing means to implement into the calibration. In addition, the acquired sample spectrum to be used as a reference spectrum contains data collection errors and has spectroscopic attributes not accounted for in the original model. Incorporation of the reference spectrum of the individual into the model thereby results in a significant potential source of error in the resulting calibration that directly translates into errors in subsequent glucose concentration predictions. In a noninvasive glucose determination, this results in an erroneous glucose concentration being reported that is used as an adjunct method for directing insulin therapy. For all of these reasons, elimination of the step of collecting and utilizing a reference sample spectrum is beneficial.

Guide

T. Blank, G. Acosta, M. Mattu, S. Monfre, Fiber optic probe guide placement guide, U.S. Pat. No. 6,415,167 (Jul. 2, 2002) and T. Blank, G. Acosta, M. Mattu, M. Makarewicz, S. Monfre, A. Lorenz, T. Ruchti, Optical Sampling Interface System For In Vivo Measurement of Tissue, U.S. patent application Ser. No. 10/170,921, (filed Jun. 12, 2002), which are both herein incorporated in their entirety by this reference thereto, describe use of a guide in conjunction with a noninvasive glucose analyzer to increase precision of the location of the sampled site resulting in increased accuracy and precision in a noninvasive glucose concentration determination. The guide is used for a period of time to increase precision in sampling throughout a period of sampling, such as a fraction of a day, one day, or a period of multiple days.

Equilibration

A number of reports exist describing the difference (or lack of difference) between traditional glucose determinations and alternative site glucose determinations. Some have recognized the potential difference as having impacts upon noninvasive glucose calibration and maintenance, see U.S. patent application Ser. No. 10/377,916. The use of heat, rubrifractants, or the application of topical pharmacologic or vasodilating agents such as nicotinic acid, methyl nicotinamide, minoxidil, nitroglycerin, histamine, menthol, capsaicin, and mixtures thereof to hasten the equilibration of the glucose concentration in the blood vessels with that of the interstitial fluid has been reported. [see Rohrscheib, Mark; Gardner, Craig; Robinson, Mark R. Method and Apparatus for Non-invasive blood analyte measurement with Fluid Compartment Equilibration, U.S. Pat. No. 6,240,306, May 29, 2001 and Robinson, Mark Ries; Messerschmidt, Robert G. Method for Non-Invasive Blood Analyte Measurement with Improved Optical Interface, U.S. Pat. No. 6,152,876, Nov. 28, 2000].

Release of nitric oxide via photo stimulation is described for use in combination with noninvasive glucose determinations as a method of equilibrating glucose concentrations in poorly perfused regions of the body with glucose concentrations of more well perfused regions of the body. [T. Blank, S. Monfre, M. Makarewicz, M. Mattu, K. Hazen, and R. Henderson, Photostimulation method and apparatus in combination with glucose determination, filed May 6, 2004.

In all of the related technology of this section, no suggestion of the use of mean centering utilizing only a reference glucose value in conjunction with a guide that eliminated the need for a spectral reference is made. Further, no suggestion is made for easing the use of a bioanalyzer such as a near-IR based noninvasive glucose analyzer through the use of a guide to reduce the need for mean centering related techniques based upon spectral references. Further, no minimization of reference glucose concentration differences has been suggested with the use of photo stimulation. Finally, to date no FDA device has been approved for the utilization by an individual or a medical professional for noninvasive glucose concentration determination.

The Problem

Physiological parameters that change the state of skin include: tissue hydration, skin temperature, volume fraction of blood in tissue, skin thickness, magnitude of absorbance features related to fat, hematocrit concentration, and surface reflectance. Many of these parameters change over a period of one or more days or over a much longer period of time such as weeks.

Changes in the state of skin alter a number of properties such as: water concentration, the concentration of other analytes such as protein, fat, keratinocytes and glucose, the scattering of skin, the absorbance of skin, the refractive indices of various layers of skin, the thickness of tissue layers, the emitted radiation from the body, the mechanical properties of tissue, magnitude of absorbance features related to water, magnitude of absorbance features related to protein, and the size and distribution of scattering centers.

Noninvasive spectra, such as a near-IR based diffuse reflectance spectrum, are representative of skin tissue properties. Since a large number of state changes each effect a large number of skin tissue properties, variations through time of noninvasive spectra of a given skin sampling site often vary in a highly nonlinear and profound manner.

Further, factor analysis based multivariate models result in abstract features. Therefore, change in state often profoundly effects multivariate model predictions.

Because near-IR based noninvasive glucose analyzers typically use multivariate analysis that is susceptible to sample state changes, the model must be robust or optionally updated. The invention herein focuses on maintenance of one or more calibrations. Calibration maintenance is a costly and time-consuming process that requires some technical skill. Elimination or automation of steps required for maintenance of a noninvasive glucose analyzer is beneficial for at least one of increasing marketability of the analyzer, increasing the number of people who may use the analyzer, reduction in time requirements associated with a glucose concentration determination, and increased precision and/or accuracy of a glucose concentration determination. Specifically, elimination of any data gathering step, such as collection of spectra, is beneficial for the above reasons. This invention provides a simple calibration maintenance method for use with a noninvasive glucose concentration analyzer.

SUMMARY OF THE INVENTION

A method and apparatus for easing the use of an optically based noninvasive analyzer is presented. More particularly, a simplified algorithm is used that removes the daily requirement of collecting and using a noninvasive spectrum to update a calibration model. In another embodiment, a guide is used to substantially reduce variation in sample probe placement in relation to a skin tissue sampling site, resulting in the ability to maintain calibration performance with the use of a reference analyte concentration, with or without the use of a reference spectrum collected nearby in time.

DETAILED DESCRIPTION OF A PREFERRED EMBODIMENT

Figure 1:
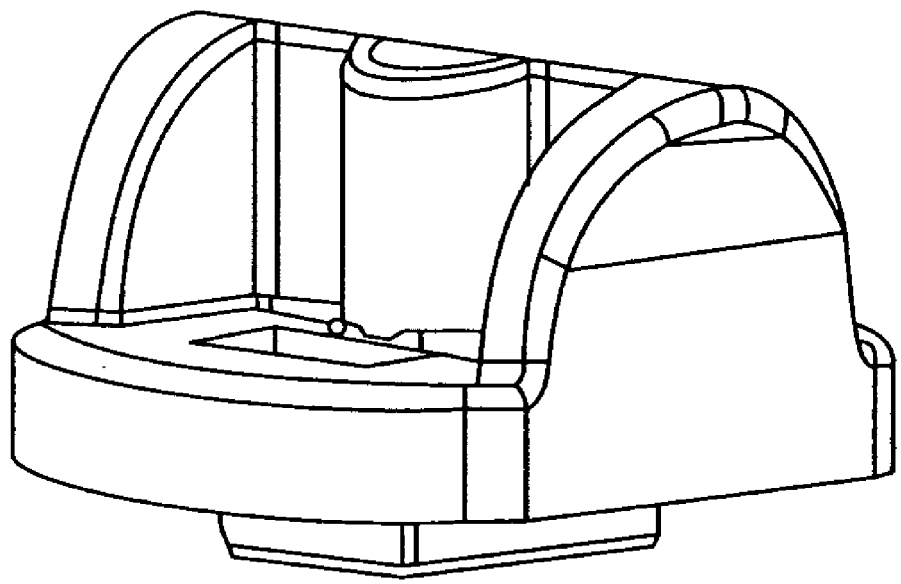
FIG. 1 shows a flat guide coupled to a plug, according to the invention.
Figure 1:
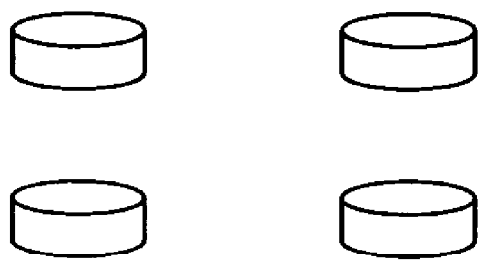
Figure 1:
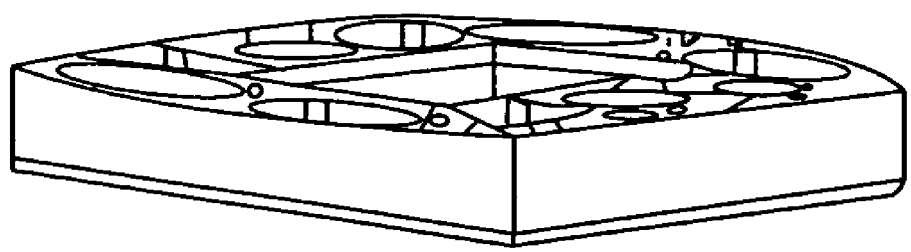

The preferred embodiment of the invention uses a near-IR based glucose concentration analyzer to obtain a spectrum of a sample site of an individual in conjunction with a model and a reference analyte concentration correction to predict/measure a glucose concentration of the subject.

As described in E. Thomas, U.S. Pat. No. 6,528,809, supra, and E. Thomas, U.S. Pat. No. 6,157,041, supra a traditional offset correction uses both a reference spectrum from the individual being tested and a direct glucose reading from the individual. The term reference spectrum herein refers to a tissue spectrum, such as an initial spectrum of a day, a spectrum from a library, or a matched spectrum, as opposed to a spectrum of a reference standard, such as an intensity standard. As discussed above, the collection of the reference spectrum has costs in terms of instrumentation requirements, software requirements, time, user proficiency, and is a potential source of error that directly manifests itself in resulting glucose predictions that is used to direct insulin therapy. For all of these reasons, elimination of the step of collecting and using a reference sample spectrum is beneficial.

The preferred embodiment provides for a method and apparatus that eliminate the step of collecting a noninvasive reference spectrum for a periodic update of the calibration model. That is, neither a reference spectrum of the individual user, a reference spectrum from a spectral library, nor a matched spectrum to the individual is used to update a model on a daily, weekly, or monthly basis. Elimination of the necessity of the reference spectrum is made possible for at least one of the following reasons:

First, the collection of a reference spectrum does not benefit the net predicted glucose concentration. Generally, the application of a reference spectrum provides an offset that is a constant. In addition, the direct reference glucose determination provides an offset that is a constant. As both offsets are a constant, a single correction using the direct glucose concentration determination accounts for the overall error that incorporates both constants. This is detailed below.

In particular, in Equation 1, $X_{measured}$ is a vector of a prediction spectrum, $W^T$ is the vector of coefficients associated with the regression model, and $y_{hat}$ is the resulting analyte (glucose) concentration prediction prior to any correction. Notably, $y_{hat}$ has an error associated with it. The prediction $y_{hat}$ is thought of as an uncorrected estimation of the glucose concentration.

$$y_{hat} = (X_{measured})W^T \quad (1)$$

The estimated $y_{hat}$ glucose concentration prediction has error for a number of reasons including instrumentation, environmental, and sampling impacts on the measured spectrum. Of particular importance are tissue volume changes that lead to a bias through changes in parameters such as the optical pathlength, absorption coefficient, and scattering coefficient.

In a first method of correcting for the error in the predicted glucose concentration, $y_{hat}$, that was reported in E. Thomas, U.S. Pat. No. 6,528,809, supra and E. Thomas U.S. Pat. No. 6,157,041, supra, a noninvasive reference spectrum, $X_{ref}$, is used to localize the measured sample spectrum. The use of the reference spectrum, $X_{ref}$, results in an offset to the predicted glucose concentration, $y_{hat}$, error equal to $y_{bias1}$, Equation 2. The new partially corrected prediction of the actual glucose concentration is referred to herein as $y'_{hat}$. Often $X_{ref}$ is a mean spectrum, but as discussed below there are a number of other sources for the $X_{ref}$ spectrum.

$$y'_{hat} = y_{hat} + y_{bias1} = (X_{measured} - X_{ref})W^T \quad (2)$$

Essentially the term $X_{ref}W^T$ results in an offset to $y_{hat}$ equal to the constant $y_{bias1}$. It is possible that this correction is sufficient to the point the $y_{hat} + y_{bias1}$ is equal to the actual glucose concentration within acceptable performance specifications. For example, the analyzer requirements may have loose accuracy requirements such as determining if the analyte concentration is high or low. This allows correction of the error to acceptable limits with only the use of a reference spectrum. However, typically the resulting reference adjusted spectrum after being applied to the model results in a relative analyte (glucose) concentration prediction that still requires an offset correction. This offset correction is performed using a direct reference glucose concentration. Typically, a direct reference glucose concentration is a traditional fingerstick glucose determination, but additional options are discussed below. The direct glucose concentration reading or reference glucose determination is here referred to as $y_{bias2}$. Combining the direct glucose concentration determination step with the bias correction step of Equation 2 results in a measured analyte (glucose) concentration, $y_{meas}$, as in Equation 3.

$$y_{meas} = y_{hat} + y_{bias1} + y_{bias2} = (X_{measured} - X_{ref})W^T + y_{bias2} \quad (3)$$

As indicated above, this first method requires collection and use of both a noninvasive reference spectrum and a reference glucose concentration.

Going back to Equation 1, it is again noted that the measured spectrum applied to the calibration model results in a glucose prediction, $y_{hat}$, that has an error associated with it. In a second method, this error is corrected by using only the direct glucose reference determination without the prior step of subtracting out a mean spectrum.

In this case, the direct reference glucose determination here referred to as $y_{err}$ provides an estimated error of the predicted glucose concentration $y_{hat}$, Equation 4 used to estimate a glucose concentration.

$$y_{meas} = y_{hat} + y_{err} = X_{measured}W^T + y_{err} \quad (4)$$

Notably, the estimated error, $y_{err}$, using this second method is seen by comparison of Equations 3 and 4 to represent both of the errors from the more complicated 2-step method above that resulted in the $y_{bias1}$ and $y_{bias2}$ terms.

An alternative embodiment of the invention is now presented that uses one or more stored reference spectra. In the methods above, it is common to refer to the reference spectrum as a mean spectrum because a common technique is to subtract out the spectrum, and this is often done with a mean spectrum. However, the reference spectrum is one of a number of spectra, including the first spectrum of a time period where the time period includes a day, week, month, or even a spectrum collected for an individual upon delivery of the instrument. Typically, the correction is performed once a day, waking day, or major fraction of a day. Instead of using the first spectrum of a time period, the average of the first n spectra of a time period is used as may a spectrum that is a linear combination of any number of time adjacent or time separated spectra of a time period. Optionally, the reference spectra originates from a data base such as a spectral library and is chosen based upon spectral features or based upon a calculation such as a Mahalanobis distance calculation. In an additional embodiment, a basis set gold standard spectrum, such as a spectrum of water, is used as the reference spectrum. The advantage of a fixed gold standard spectrum is that it is collected in a controlled environment and is digitally stored in the analyzer for use in subsequent model updates.

Still an additional embodiment of the invention uses a near-IR based glucose concentration analyzer to obtain a spectrum of a sample site of an individual in conjunction with a guide, a model, and a reference analyte concentration to predict measure a glucose concentration of the individual.

Spectrometer light throughput is effected by a number of factors, including environmental states and the state of a sample. In addition, changes in environmental states and changes in the state of the body result in dynamic changes to a living tissue sample site. Examples of change that alter the tissue state include temperature changes and/or distributions, localized pressure changes or distributions, water movement, glucose movement, and changes in body composition such as protein, fat, and hematocrit. These changes affect the chemical and physical attributes of the body. Physical changes include localized and/or regional changes in the refractive index, absorption coefficient, anisotropy, and scattering coefficient that affect probing photon penetration, radial transport, and optical pathlength. Combined, these state changes result in a high-degree of nonlinearity being observed in noninvasive spectra. Many of these changes have a large dependency on the positioning of an optical sampling probe, that includes excitation and/or collection elements of a spectrometer, relative to the sample volume.

The physiology of skin is not homogeneous. The chemical and physical make-up of skin depends upon the position of the skin. Many differences in skin structure with position exist, including thickness of skin layers and the skin physical constituents. Noninvasive spectra of the body are dependent upon the sample site. For example, the spectra of a forearm skin tissue sample is different depending upon where on the forearm the skin is sampled. For example, a skin sample varies as a function of position in terms of constituents such as water, fat, and protein and in properties such as the scattering coefficient.

Guide

In its broadest sense, a guide is an element that limits positioning of a sample probe relative to a sample site. The guide couples an input and output element to a targeted tissue volume, thereby controlling and reducing spectral variation, and results in decreased error in a determined analyte concentration. A guide is illustrated as one-half of a lock and key mechanism where the guide lock limits the positioning of the sample probe (key) relative to the sample site. A guide aids in the reproducibility of locating sampling and collection elements, such as a sample probe and fiber optics of a noninvasive spectrometer based analyzer, in relation to a sampling site and is beneficial to a noninvasive analyte concentration determination due to the associated reduction of nonlinear variability. A guide has been taught in U.S. Pat. No. 6,415,167 (Jul. 2, 2002), and U.S. patent application Ser. No. 10/170,921 (filed Jun. 12, 2002), which are both herein incorporated in their entirety by this reference thereto.

A number of guide and attachment apparatus are described herein. Preferably, the attachments have the same interface so that a single guide element is used with each attachment. Similarly, it is preferable to have each of the pieces of apparatus that attach to an attachment have the same interface. For example, the guide and a reference sample preferably have the same interface so that they both couple to a sample probe. A common interface allows any of the guides or a reference to interface with any of the attachments, such as the plug, photonic stimulator, sample module, or miniaturized source.

Lock (Guide)

A sample site varies between individuals in terms of circumference or radius of curvature. For body parts, such as an abdominal region or a finger, the radius of curvature may range from flat to 0.375 inch, respectively. Even within a body part, the radius of curvature varies between individuals. For example, some individuals have small diameter arms while others have larger diameter arms. Matching the shape of a guide to the structure of the sample site results in increased precision of subsequent optical sampling.

Examples of guides are those that have flat sample interfaces and those with a 6.0 inch, 4.5 inch, and 3.0 inch radius of curvature. FIG. 1 presents a guide element with a flat radius of curvature. For the case of an arm sampling site, the skinnier the arm the smaller the radius of curvature of the optimal guide. The guide presented in FIG. 1 is presented in relation to a plug, which is one of the guide attachments discussed below. A core feature of the guide element is that is makes up one-half of a lock and key combination. That is, a surface exists that reproducibly guides the other half of a lock and key element into a reproducible position. In this case, the lock element is in the guide, but alternatively it is in the attachment. In this case, the lock element is a hole in the guide that is roughly rectangular with two opposing sides each having rounded shapes. The rectangular shape limits rotational alignment. Preferably, the guide would not have rotational freedom. For instance, the pictured guide has C2 symmetry allowing it to be rotated by 180 degrees and still having the same shape. This rotational freedom is obtained by many means, such as by flattening one of the round ends. In a second case, the lock element has pins extending from it that interface into associated holes in the key (attachment) element to position the key relative to the guide reproducibly.

Many lock element shapes are readily used. Examples include virtually any geometrically shaped hole or any shape (not necessarily a hole) that provides reproducible positioning while, preferably, preventing freedom of rotation. In the particular guide elements presented, optional additional holes or divots are pictured. The function of these is primarily to reduce weight, minimize surface abnormalities, such as sink marks on the sampling site, and to maintain strength while limiting the twisting freedom of the guide. An additional optional component pictured on these guides are magnets. The magnets are used to control contact force and/or to aid in alignment of the lock and key mechanism. In the guide pictured, optional opposing pole magnets are also placed into the plug. Of the paired magnets, one half of the pair is optionally a metallic substance, such as sheet metal or stainless steel, which reduces cost and/or weight. Many additional mechanical structures and will be obvious to those skill in the art that allow the lock element to interface with the guide element.

The guide is attached to a sample site with a device, such as a band, strap, hook and loop technology, or preferentially with a double sided adhesive. Commonly, the adhesive is firmly placed onto the sample site and then the guide is visually aligned onto the adhesive. This sequence reduces separation events of the adhesive from the sample site. Optionally, the adhesive is attached to the guide and the pair is placed into contact with the sample site as a unit. This eases alignment of the guide to the adhesive. Optionally, the adhesive comes to the user already attached to the guide element. The guide and adhesive are semi-permanently and removeably attached to the sampling site. The guide is typically left in place for the remainder of a sampling period such as one waking day or the length of a data collection period, such as 2, 4, or 8 hours.

An optional intermediate layer or guide extension is used between the guide and the double sided adhesive that attaches to the sampling site. Essentially, this is a semi-flexible material such as acetate. The material allows some flexibility to allow the sample site skin to stretch. This reduces sampling transients resulting from movement of the subject. Conversely, in subjects with poor turgor, the skin flexes too much and a more rigid insert, such as a plastic film is used.

The guide is preferentially formed out of a thermoplastic, such as a polycarbonate or a polyurethane. However, many materials will be obvious to those skilled in the art. Because the guide is in contact with the sampling site (sometimes with an intermediate adhesive), the thermal properties of the guide become important. Typically, the guide is non-thermally conductive to reduce sampling site temperature gradients. However, in some cases a thermally conductive guide is preferential, such as when heat flow to or from the sample site is desired. The guide material is preferentially biocompatible.

Preferentially, the guide is optically coupled to the sampling site through the use of an index of refraction matching medium such as a fluoropolymer, a fluorocompound, Fluorinert, FC-40, FC-70, or equivalent.

Key (Attachment)

The other half of the guide lock and key mechanism is herein referred to as an attachment to the guide element. Examples of attachments to the guide include a plug, a photonic stimulator, a miniaturized source, and the tip of a sample module of a spectrometer. An example of each of these attachments is provided below.

A plug attachment is presented in FIG. 1 coupled to a guide. The plug functions to accomplish at least one of hydration of the sampling site by occlusion, protection of the sampling site from physical perturbation, protection of the sampling site from contamination, alignment of the guide, and allowing an aesthetic appearance, such as a watch, ring, or graphical symbol. The pictured plug has two protruding elements with a cross support designed for ease of gripping. Optionally, the plug is made to look or function like a wristwatch that may or may not have a band that looks like a watchband with it. In an alternative embodiment, the plug is miniaturized to resemble a decorative object, such as a ring.

The pictured plug in FIG. 1 has an optional central tunnel. This tunnel is used in the initial placement of the guide. In this method, a double sided adhesive strip is attached to the sampling site. The adhesive strip has an opening in it that is slightly larger than the optical probing element. After an adhesive is placed onto the arm, the guide is attached to the plug and slid down a guiding rod to the adhesive so that the optical path is centered in the cutout on the adhesive. Essentially, the rod through the plug and guide is used as a sighting mechanism.

Figure 2:
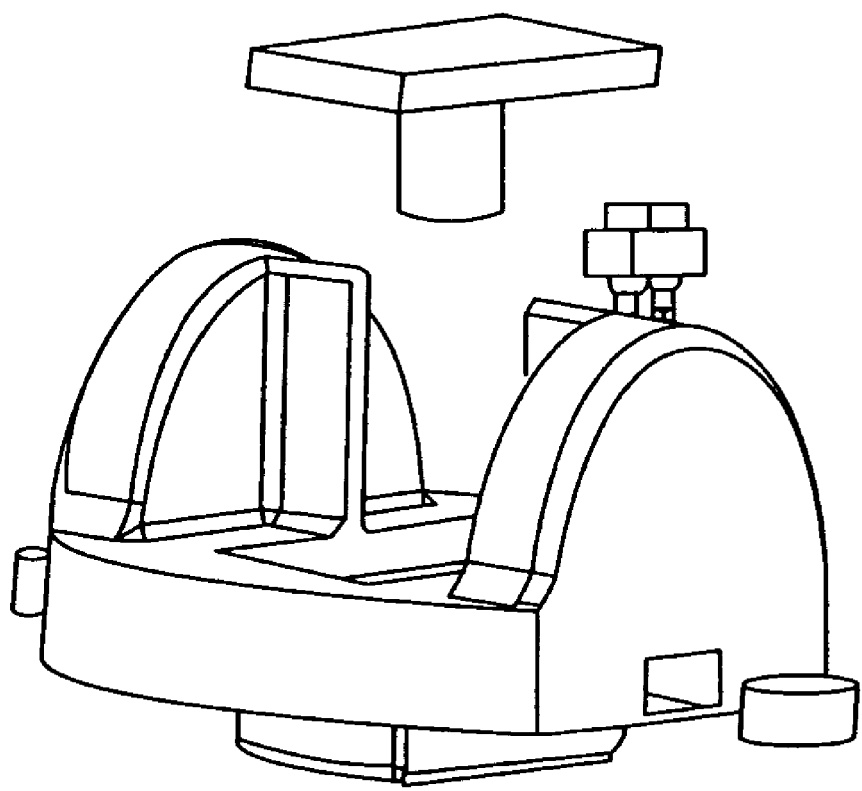
FIG. 2 presents an LED attachment coupled to a plug with a 4.5 inch radius of curvature guide, according to the invention.
Figure 2:
Figure 2:
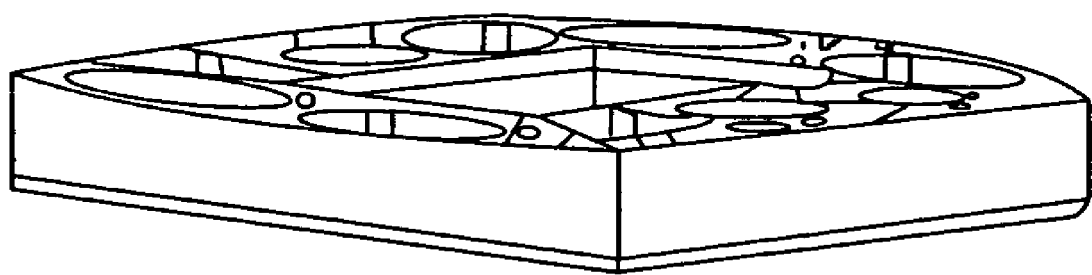

A photonic stimulator attachment is presented in FIG. 2 coupled to a guide with a 4.5 inch radius of curvature sample interface. Photo-stimulation at or near at least one sample site is used to enhance perfusion of the sample site leading to reduced errors associated with sampling. Increased perfusion of the sample site leads to increased volume percentages of the target analyte and/or allows the blood or tissue constituent concentrations to more accurately and/or precisely track corresponding sample constituents in more well perfused body compartments or sites, such as arteries, veins, or fingertips. In one embodiment, analysis of the photo-stimulated site is used in conjunction with glucose analyzers to determine the glucose analyte concentration with greater ease, accuracy, or precision and allows determination of the analyte concentration of another non-sampled body part or compartment. This technology is described in a U.S. patent application Ser. No. 10/841,200 and is herein incorporated in its entirety by this reference thereto.

Figure 3:
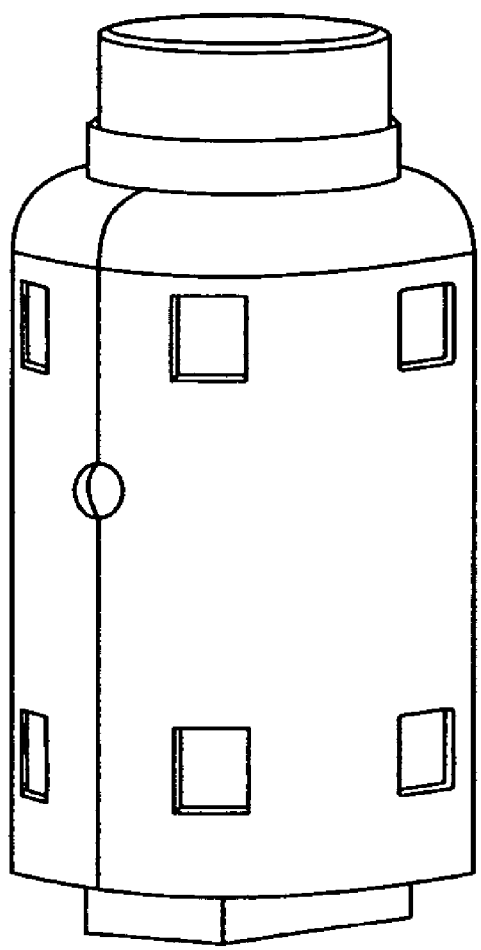
FIG. 3 presents a miniaturized source attachment coupled to a 6.0 inch radius of curvature guide, according to the invention.
Figure 3:
Figure 3:
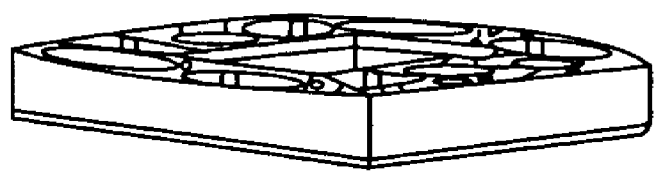

A sample module is presented in FIG. 3 coupled to a guide with a 6.0 inch radius of curvature sample interface. Sample modules are described in U.S. patent application Ser. No. 10/472,856 filed Sep. 18, 2003. A sample module is preferably part of an analyzer, the analyzer additionally comprising a base module and a communication bundle. The sample module is attached continuously or semi-continuously to a human subject and collects spectral measurements that are used to determine a biological parameter in the sampled tissue. The preferred target analyte is glucose. The preferred analyzer is a near-IR based glucose analyzer for determining the glucose concentration in the body.

Figure 4:
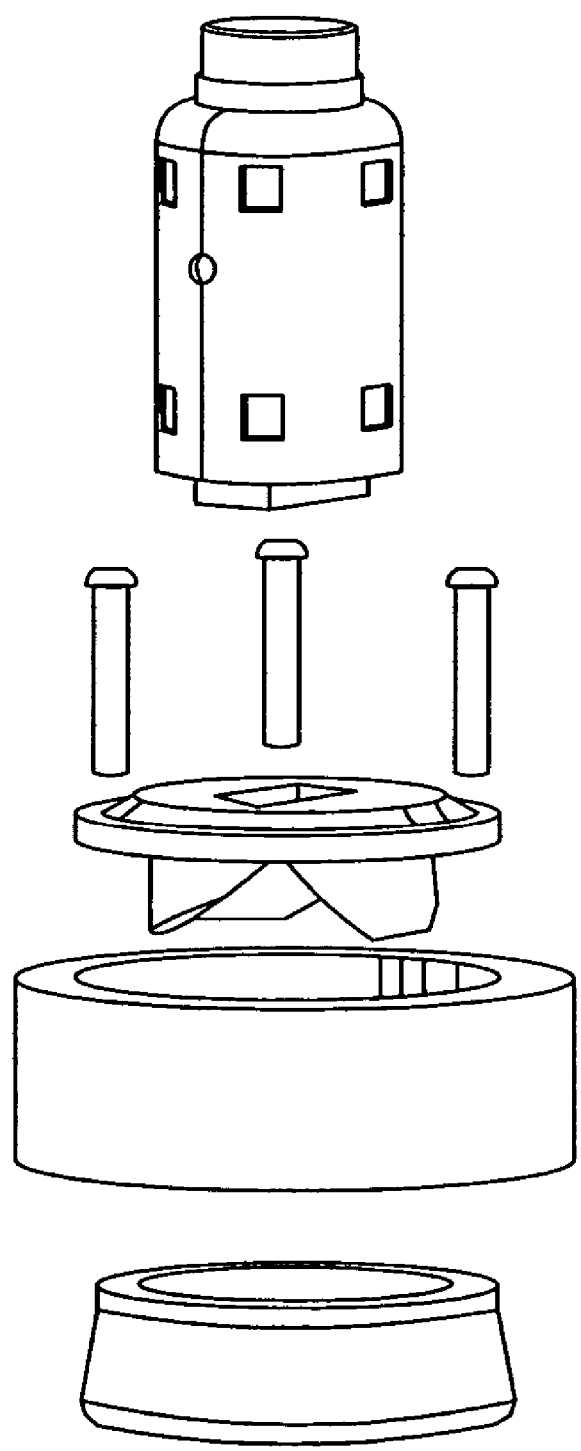
FIG. 4 presents a miniaturized source attachment coupled to a flat guide, according to the invention.

A miniaturized source attachment is presented in FIG. 4 in combination with a reference guide element. A reference element is used to provide a signal representative of the current state of the analyzer. Preferably, the reference element is contained in an element that has an interface that is functionally identical to the guide interface so that the reference couples to a sample module or a miniaturized source in the same manner as the guide.

Guide Data

Figure 5:
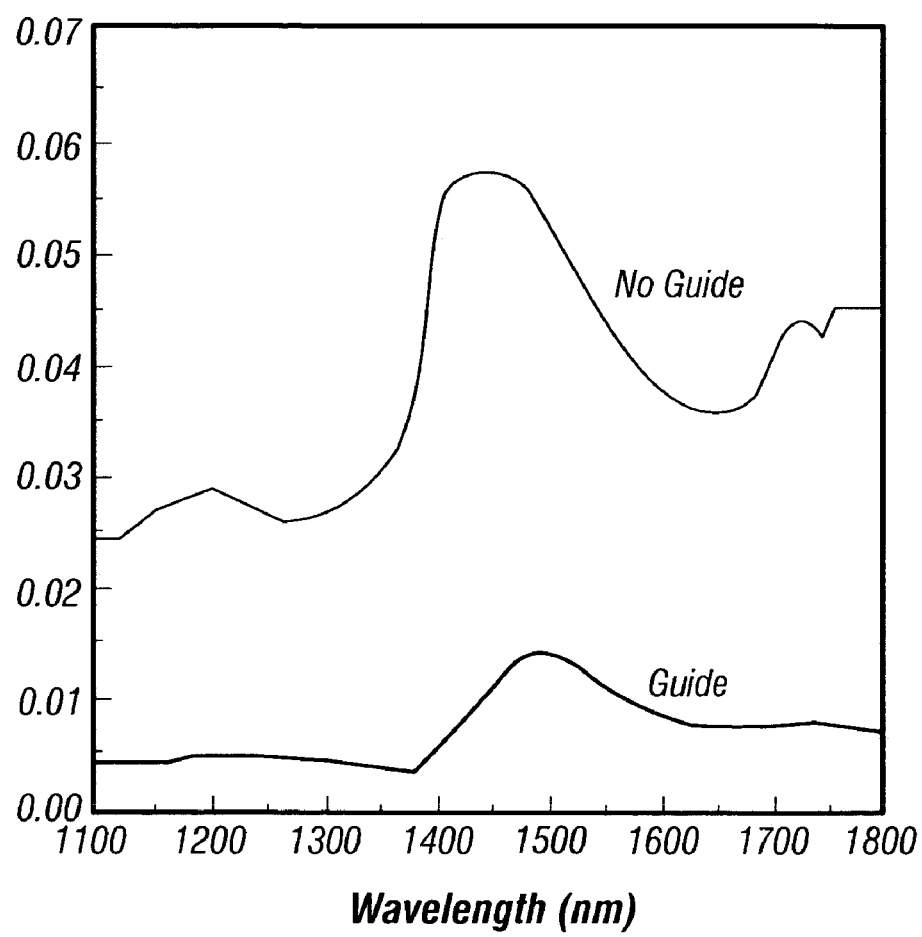
FIG. 5 presents spectral variance with and without a guide, according to the invention.

Standard deviations of a series of near-IR noninvasive spectra of an arm of a single individual are presented in FIG. 5 for spectra collected with a guide 501 and without a guide 502. The standard deviation in absorbance units are observed to be much smaller with the use of a guide. Those skilled in the art will recognize the deviations as dominated by variations due to pathlength and the probed water concentration with smaller variations being related to protein, fat, and temperature. Hence, the guide increases the precision of locating the optical probe in relation to the sample site that in turn, due to reduction in sample variation with position, result in a smaller variation in the spectral readings.

EXAMPLE

Figure 6:
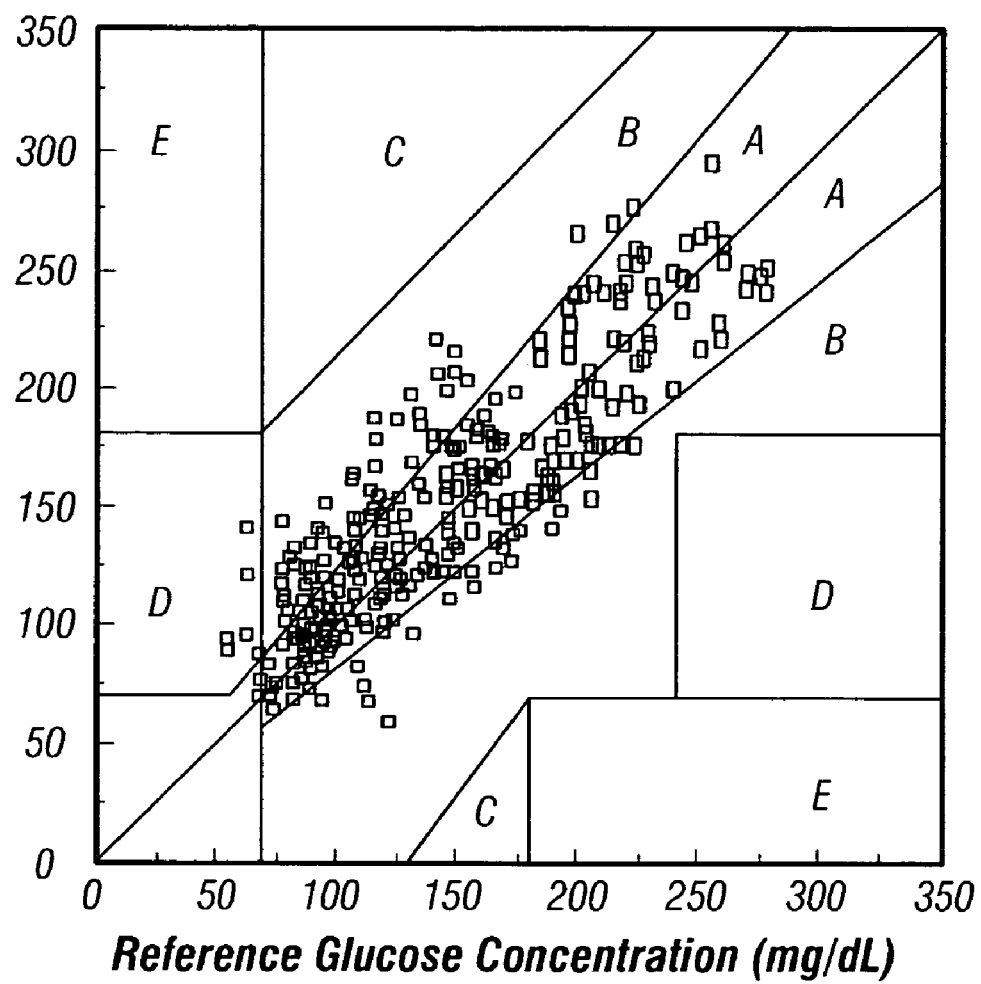
FIG. 6 presents prediction results overlaid onto a Clarke error grid, according to the invention.

An example data set of noninvasive glucose concentration prediction is presented in FIG. 6. These representative data are processed using the preferred model correction technique described above that uses only a direct glucose reference concentration and does not use a noninvasive (or related) reference spectrum. The instrumentation used to collect the calibration data includes three identically configured near-IR based analyzers configured with a tungsten halogen source, excitation guiding optics, a bandpass filter, collection guiding optics, a slit, a grating, an array detector, and associated electronics. A guide is placed onto each subject at the beginning of a given day for all measurements taken in the calibration and subsequent prediction measurements. All subjects underwent one or more glucose profiles over a period of at least one day. The calibration is built with a total of eight subjects, using the calibration instruments to collect 241 samples over a period of two months. A model is built with the data utilizing spectra from 1200 to 1800 nm preprocessed with a 27-point Savitsky-Golay first derivative. Outlier detection routines include modules for detecting and eliminating samples with poor surface contact between the optics and the sampled site, samples with large tissue transients, and samples with undue tissue distortion. A multivariate partial least squares model is used. Prediction spectra are collected with a similar glucose analyzer with differences only in the mechanism that holds the excitation and collection optics. The prediction spectra were collected over a five week period initiated seven months after the end of collection of the calibration data. The prediction data set included spectra collected from twenty-one test subjects on three instruments resulting in 368 prediction spectra. The model generated with the calibration data set was employed without modification in a blind fashion. An offset correction was used that employed a glucose reference concentration collected with the first sample of a given day. No reference spectrum from any of the prediction spectra were used in the prediction, nor was any noninvasive spectrum or synthesized noninvasive spectrum used in any phase of this prediction data set. Again, a reference glucose concentration is used to update the model for subsequent prediction of a glucose concentration with a noninvasive analyzer without the use of a corresponding noninvasive reference spectrum. The resulting predictions presented in FIG. 6 are overlaid onto a Clarke error grid. A total of 98.7% of the resulting glucose concentration predictions fell within the clinically acceptable 'A' or 'B' region of the Clarke error grid, and the resulting standard error of prediction was 26.3 mg/dL. This clearly demonstrates efficacy of the analyzer. Notably, the prediction performance is virtually identical to the calibration performance that resulted in 100% of the glucose concentration determinations falling within the 'A' or 'B' region of the Clarke error grid and had a standard error of calibration of 27.0 mg/dL.

In the methods described herein, it is common to refer to a reference spectrum as a mean spectrum because a common technique is to subtract out the spectrum and this is often done with a mean spectrum. However, an optional reference spectrum includes one of a number of spectra, including the first spectrum of a time period where the time period includes a day, week, month, or even a spectrum collected for an individual upon delivery of the instrument. Typically, the correction is performed once a day, waking day, or major fraction of a day. Alternatively, the removed spectrum is the first spectrum of a time period, the average of the first n spectra of a time period is used, or a spectrum that is a linear combination of any number of time adjacent or time separated spectra of a time period. In yet another embodiment, the reference spectrum is from a data base, such as a spectral library, and is chosen based upon spectral features or based upon a calculation, such as a Mahalanobis distance calculation. For example, a gold spectrum is used as described above.

In the methods above, the direct reference analyte concentration is typically a capillary based blood glucose determination performed with traditional enzymatic, electro-enzymatic, or colorimetric means. However, the reference glucose concentration is alternatively generated by a minimally invasive glucose meter or a noninvasive meter. Generally, an FDA approved reference method is used.

Although the invention is described herein with reference linear models, it is recognized that a non-linear model, such as a neural network, is also applicable to analyte concentration estimation.

Although the invention is described herein with reference to the preferred embodiments, one skilled in the art will readily appreciate that other applications may be substituted for those set forth herein without departing from the spirit and scope of the present invention. Accordingly, the invention should only be limited by the Claims included below.

The invention claimed is:

1. A noninvasive method for estimating a biological attribute concentration in human tissue of a tested subject, comprising the steps of:

generating a model used for estimating a current or past value, wherein said step of generating uses noninvasive spectra and associated reference concentrations;

adjusting said model with at least one direct reference measurement and without use of a corresponding reference spectrum;

collecting at least one noninvasive spectrum of said tissue of said tested subject with an analyzer;

estimating said biological attribute of said specific subject using said adjusted model; and displaying said estimated biological attribute.

2. The method of claim 1, further comprising a guide wherein said guide replaceably couples said analyzer to said human tissue.

3. A noninvasive method for measuring a biological attribute of human tissue of a tested subject, comprising the steps of:

providing an apparatus for measuring light throughput, said apparatus comprising an energy source emitting infrared energy at multiple wavelengths, an input element, an output element, and a spectrum analyzer;

coupling said input and output elements to said human tissue;

irradiating said tissue through said input element with multiple wavelengths of infrared energy with resulting absorption of at least some of said wavelengths;

collecting at least a portion of the non-absorbed infrared energy with said output element;

determining the intensities of said infrared energy;

generating a model used for estimating a current or past value, wherein said step of generating uses calibration noninvasive spectra and calibration reference concentrations;

adjusting said model with at least one direct reference measurement and without use of a corresponding reference spectrum;

collecting at least one prediction noninvasive spectrum of said tissue of said tested subject; and estimating said biological attribute of said specific subject using said adjusted model; and displaying said biological attribute.

* * * * *